(12) United States Patent
Schieven (10) Patent No.: US 9,592,315 B2
(45) Date of Patent: Mar. 14, 2017

(54) PLASMA INJECTION AIR FILTRATION AND DISINFECTION SYSTEM

(71) Applicant: Johannes Schieven, Abbotsford (CA)

(72) Inventor: Johannes Schieven, Abbotsford (CA)

(*) Notice: Subject to any disclaimer, the term of this patent is extended or adjusted under 35 U.S.C. 154(b) by 0 days.

(21) Appl. No.: 14/734,216

(22) Filed: Jun. 9, 2015

(65) Prior Publication Data

US 2015/0283283 A1    Oct. 8, 2015

Related U.S. Application Data (63) Continuation-in-part of application No. 13/565,605, filed on Aug. 2, 2012, now Pat. No. 9,050,556.

(Continued)

(51) Int. Cl.
   *A61L 2/00*     (2006.01)
   *B01J 19/08*    (2006.01)
   (Continued)

(52) U.S. Cl.
   CPC .............. *A61L 9/22* (2013.01); *A61L 2/14* (2013.01); *B01D 53/32* (2013.01);
   (Continued)

(58) Field of Classification Search
   CPC .. A61L 9/00; A61L 9/03; B01D 53/34; B03C 3/00
   (Continued)

(56) References Cited

U.S. PATENT DOCUMENTS 2,660,559 A    8/1949  Prime
3,696,269 A   10/1972  Hochheiser et al.
(Continued)

FOREIGN PATENT DOCUMENTS

WO          9614149        5/1996
WO    WO 2007/089887 A2 *  8/2007    .............. B01J 19/08
(Continued)

OTHER PUBLICATIONS

Tetsuji Oda, Koichi Ono and R. Ono, Dept.Electr.Eng., The University of Tokyo, Short Gap Non-Thermal Plasma Performance to Decompose Dilute Trichloroethylene, ICESPX-Australia 2006, Paper 5C1.
SULFATREAT, The original hydrogen sulfide scavenger, Product Bulletin, www.sulfatreat.com.
SULFATREAT: The SULFATREAT Process, http://www.sulfatreat.com/The%20SULFATREAT%20Process/; Jan. 18, 2011.
G. Kamgang-Youbi, J.M. Herry, T. Meylheuc, J.L. Brisset, M.N. Bellon-Fontaine, A. Doubla and M. Naitali, "Microbial inactivation using plasma-activated water obtained by gliding electric discharges", The Society for Applied Microbiology, Letters in Applied Microbiology, 2009, 6 pages.
(Continued)

*Primary Examiner* — Monzer R Chorbaji
(74) *Attorney, Agent, or Firm* — Schacht Law Office, Inc.; Dwayne Rogge (57) ABSTRACT

Disclosed herein is a plasma reactor insert assembly having in one example an outer casing comprising; a fluid inlet; a fluid outlet; an electric power input; and electric power connector; a transformer bracket coupled to the outer casing; at least one step-up transformer attached to the transformer bracket. The insert in electric communication with the electric power connector; a plurality of substantially parallel dielectric tubes in electric communication with the transformer; at least one grounded plate positioned between each dielectric tube with a fluid gap there between, and; wherein there is no fluid path between the fluid inlet and the fluid outlet except by passing between one of the dielectric tubes and one of the grounded plate. In one form, each grounded plate is v-shaped or arcuate v-shaped in cross-section. A method for disinfecting or sanitizing using the plasma reactor is also described.

17 Claims, 8 Drawing Sheets

Related U.S. Application Data (60) Provisional application No. 61/514,588, filed on Aug. 3, 2011.

(51) Int. Cl.
| | | |
|---|---|---|
| *A61L 9/00* | (2006.01) | |
| *H05F 3/00* | (2006.01) | |
| *B03C 3/00* | (2006.01) | |
| *A61L 9/22* | (2006.01) | |
| *B01D 53/32* | (2006.01) | |
| *A61L 2/14* | (2006.01) | |

(52) U.S. Cl.
CPC ...... *A61L 2202/14* (2013.01); *A61L 2209/111* (2013.01); *A61L 2209/212* (2013.01); *A61L 2209/213* (2013.01); *B01D 2257/708* (2013.01); *B01D 2257/90* (2013.01); *B01D 2257/91* (2013.01); *B01D 2259/4508* (2013.01); *B01D 2259/818* (2013.01); *Y10T 29/49117* (2015.01)

(58) Field of Classification Search
USPC .... 422/22, 186.4, 186.1, 305–306, 906–907; 204/164, 176, 280, 288.1; 55/360, 55/DIG. 38; 95/57, 78, 267; 96/15, 60
See application file for complete search history.

(56) References Cited

U.S. PATENT DOCUMENTS

| | | |
|---|---|---|
| 4,690,803 A | 9/1987 | Hirth |
| 4,954,320 A | 9/1990 | Birmingham et al. |
| 5,552,125 A | 9/1996 | Chamblee et al. |
| 5,630,990 A | 5/1997 | Conrad et al. |
| 6,139,809 A | 10/2000 | Rodden |
| 6,500,387 B1 * | 12/2002 | Bigelow .................. A61L 9/20 250/432 R |
| 6,635,153 B1 | 10/2003 | Whitehead |
| 6,723,293 B2 | 4/2004 | Jensen |
| 7,294,262 B2 | 11/2007 | Tadlock |
| 7,767,167 B2 | 8/2010 | Keras |
| 2005/0045552 A1 | 3/2005 | Tadlock |
| 2006/0204409 A1 | 9/2006 | Son |
| 2006/0251550 A1 | 11/2006 | Keras |

FOREIGN PATENT DOCUMENTS

| | | |
|---|---|---|
| WO | WO2007089887 | 8/2007 |
| WO | WO2008055337 | 5/2008 |

OTHER PUBLICATIONS

J. Jeon, T.G. Klaempfl, J.L. Zimmermann, G.E. Morfill and T. Shimizu, "Sporicidal properties from surface micro-discharge plasma under different plasma conditions at different humidities", New Journal of Physics, Oct. 7, 2014, 15 pages, IOP Publishing Ltd and Deutsche Physikalische Gesellschaft.

Danny Bayliss, "Cold plasma: Applications and future perspectives within the food and drink industry", Campden BRI, 29 pages, United Kingdom.

Dana Ziuzina, Sonal Patil, Patrick J. Cullen, Kevin Keener and Paula Bourke, "Atmospheric Cold Plasma Inactivation of *Escherichia coli, Salmonella enterica Serovar Typhimurium* and *Listeria Monocytogenes* Inoculated on Fresh Produce", Dublin Institute of Technology, School of Food Science and Environmental Health, 2014, 29 pages.

N.N. Misra, Shashi Fishor Pankaj, Tony Walsh, Finbarr O'Regan, Pauls Borke, "In-package nonthermal plasma degradation of pesticides on fresh produce", Dublin Institute of Technology, School of Food Science and Environmental Health, Dec. 2, 2014, 15 pages.

\* cited by examiner

FIG. 27

PLASMA INJECTION AIR FILTRATION AND DISINFECTION SYSTEM

This disclosure claims priority to and is a Continuation in Part of U.S. patent application Ser. No. 13/565,605 filed on Aug. 2, 2012 which issues on Jun. 9, 2015 as U.S. Pat. No. 9,050,556 incorporated herein by reference. U.S. patent application Ser. No. 13/565,605 claimed priority to U.S. Provisional Patent Application 61/514,588 filed on Aug. 3, 2011 and incorporated herein by reference.

BACKGROUND OF THE DISCLOSURE

Field of the Disclosure

This application relates to the field of applying plasma (oxygen radicals, hydroxyl radicals, ions, ozone) activated water (PAW) and/or plasma activated gas (PAG) formed by reacting a humidity controlled airflow within a plasma reactor to rapidly oxidize contaminants (odors, bacteria, viruses, etc.) in air/gas/liquids or on surfaces to which the airflow is directed.

SUMMARY OF THE DISCLOSURE

Disclosed herein is a plasma reactor assembly comprising in one form: a casing comprising; a fluid inlet for of air, Oxygen (O2), Nitrogen (N2), Hydrogen Peroxide (H2O2), Water (H2O), etc.; a fluid outlet for PAG or PAW; an electric power input; an electric power connector; at least one step-up transformer; the transformer in electric communication with the electric power connector; a plurality of substantially parallel dielectric tubes in electric communication with the transformer; at least one arcuate v-shaped electrode divider positioned between each dielectric tube with an fluid gap between each electrode divider and each adjacent dielectric tube, and; wherein there is no fluid path between the fluid inlet and the fluid outlet except between the dielectric tubes and the electrode dividers.

The plasma reactor assembly may be arranged wherein each dielectric tube in turn comprises: an outer ceramic tube; an inner metal electrode tube; and a central high voltage lead.

The plasma reactor assembly may be arranged wherein the casing comprises: an upper unit containing the transformer bracket and transformers therein; a lower unit comprising the dielectric tubes and the electrode dividers therewithin, and; a releasable physical connection and a releasable electrical connection there between the upper unit and the lower unit.

The plasma reactor assembly may be arranged wherein the casing comprises a first half of a bayonet style coupling operatively configured to couple to a second half of the bayonet style coupling which is provided on a cabinet housing.

The plasma reactor assembly may further comprise: a cabinet door, and; an door switch operatively configured to allow electricity to be provided to the electric power inlet of the outer casing only when the cabinet door is closed.

The plasma reactor assembly may be arranged wherein each transformer comprises a high frequency, high voltage output to the dielectric tubes.

The plasma reactor assembly may be arranged wherein the casing has a shape and size identical to the housing of an existing chemical or barrier filter to provide a retrofit thereto when electrically connected to a power source.

The plasma reactor assembly may be arranged wherein: the fluid inlet and fluid outlet of the casing is in-line with a vent stack of a production process to treat the fluid passing there through by way of rapid oxidation.

The plasma reactor assembly may be arranged wherein the fluid outlet of the casing is tangential to a vent stack of a production process to provide plasma into the vent stack which in turn reacts with the fluid passing there through by way of rapid oxidation.

The term "production process" is used herein to cover airflow from a manufacturing process, HVAC system, food storage location, air supply for hospitals/airports and other locations, residence air supply, and equivalent locations and applications.

The plasma reactor assembly may be arranged wherein the fluid outlet of the outer casing in fluid communication with a chemical reaction or catalyst filter selected from chemical reaction filters which are regenerated by contact with ozone produced by the dielectric tubes.

The plasma reactor assembly may be arranged wherein the outer casing is substantially cylindrical.

A method for replacing a chemical or barrier filter with a plasma reactor assembly is also disclosed. The method comprising the step of: providing plasma reactor having an outer casing comprising; a fluid inlet air, Oxygen (O2), Nitrogen (N2), Hydrogen Peroxide (H2O2), Water (H2O), etc.; a fluid outlet for PAG or PAW; an electric power input; an electric power connector. The method may also include the steps of; providing at least one step-up in electric communication with the electric power connector; providing a plurality of substantially parallel dielectric tubes in electric communication with the transformer; providing at least one arcuate v-shaped electrode divider positioned between each dielectric tube with a fluid gap between each electrode divider and each adjacent dielectric tube, wherein there is no fluid path between the fluid inlet and the fluid outlet except between the dielectric tubes and the electrode dividers; removing an existing chemical or barrier filter; installing the plasma reactor into the space vacated by the removed chemical or barrier filter; and connecting a power supply to the plasma reactor.

A method for disinfecting or sanitizing is also disclosed, comprising the step of: providing a casing comprising; a fluid inlet for air, Oxygen (O2), Nitrogen (N2), Hydrogen Peroxide (H2O2), Water (H2O), etc.; a fluid outlet for PAG or PAW; an electric power input; an electric power connector. The term disinfecting generally intended to mean completely eliminating/killing/destroying unwanted contaminates, whereas the lesser level "sanitizing" may be sufficient. The method may also include the steps of: providing at least one step-up transformer in electric communication with the electric power connector; providing a plurality of substantially parallel dielectric tubes in electric communication with the transformer; providing at least one arcuate v-shaped electrode divider positioned between each dielectric tube with a fluid gap there between, and; wherein there is no fluid path between the fluid inlet and the fluid outlet except between the dielectric tubes and the electrode dividers; and directing a fluid output of the fluid outlet to a matter to be disinfected, either solid, liquid, or gas. This step may be implemented with or without recirculation.

The method may include a step of manipulating the humidity of fluid entering the fluid inlet.

The method for disinfecting may further comprise a step of adding reactants to the fluid output or fluid input, the reactants may be selected from the list consisting of Oxygen (O2), Nitrogen (N2), Hydrogen Peroxide (H2O2), Water (H2O), etc.

The method for disinfecting may further comprise the step of controlling the temperature of the fluid output and/or input.

The method for disinfecting may be implemented wherein the disinfecting step includes a step of applying the fluid output to chemicals for improved oxidation. The method for disinfecting may be implemented wherein the disinfecting step includes a step of applying the fluid output to chemicals or catalysts for improved oxidation.

DESCRIPTION OF THE PREFERRED EMBODIMENTS

This disclosure relates to the field of oxidizing/disinfecting/sanitizing contaminates in or on gasses/liquids/solids by way of plasma activated water (PAW) wherein the PAW and/or plasma activated gas (PAG) is formed by cold plasma, or NTP (Non-Thermal Plasma). Since developing the plasma injection technology and treating more than 2,000,000 m3/h (median 17,000 m3/h or 10,000 cfm per system) of air world-wide, this technology has improved to become the most efficient, compact and economical available for many applications.

Figure 5:
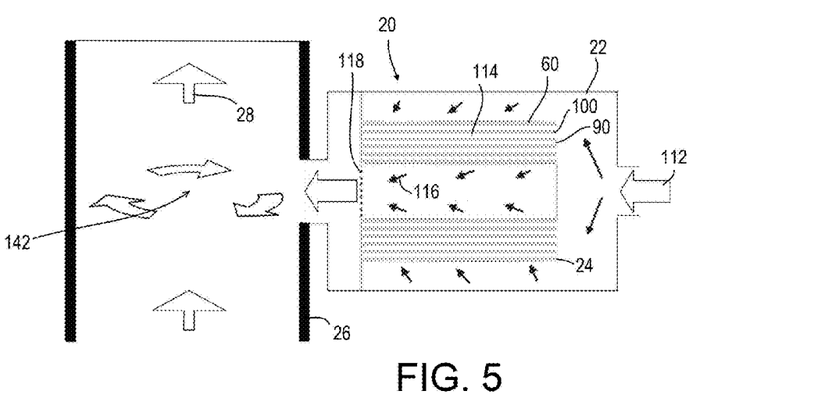
FIG. 5 is a highly schematic view of one mode of use of the disclosure.

In one example described in reference to FIG. 5, using similar plasma reactors to treat non-humidity controlled air, a small housing of 40×70×75 cm is provided injecting 2,000 m3/h of PAW/PAG, converted from clean ambient air with the plasma-injector 22, utilized to inject plasma into a production stack 26 with process airflow 20,000 m3/h and controlling the odor with only 6 kW.

In one form, no chemicals, biomaterial, masking agents are required to clean the air, form the PAW, and disinfect a surface and no significant obstructions are present in the process airflow. One example of this is shown in FIG. 5 where the plasma reactor 24 disposes plasma into the stack 26 through an outlet 118. The plasma thus creates a fast oxidation region 142 within the stack 26, forming PAW within the airflow 28.

Figure 7:
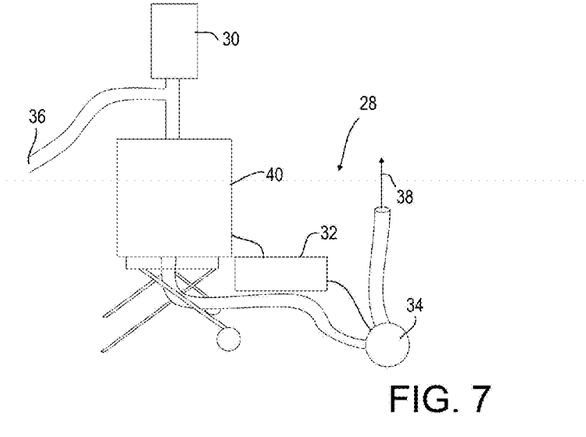
FIG. 7 is a highly schematic view of one operation example of the disclosure.

One disclosed step in the method of using the disclosed odor control and disinfecting method and apparatus may be to evaluate odor reduction and/or oxidation and/or disinfecting requirements with a small pilot demonstration/evaluation unit 28, shown in FIG. 7, at the production site and provide odor dispersion and disinfection modeling with independent odor labs to demonstrate and provide the required efficiency according local regulations. The demonstration unit 28 allows for testing and evaluation. A full-scale installation would generally then follow.

Figure 1:
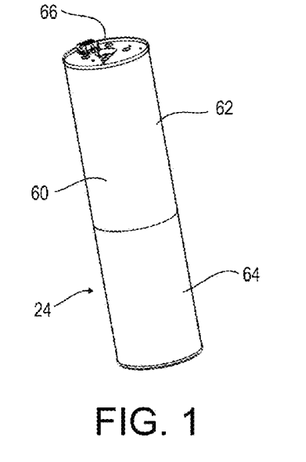
FIG. 1 is an isometric view of one example of a plasma reactor as described herein.
Figure 4:
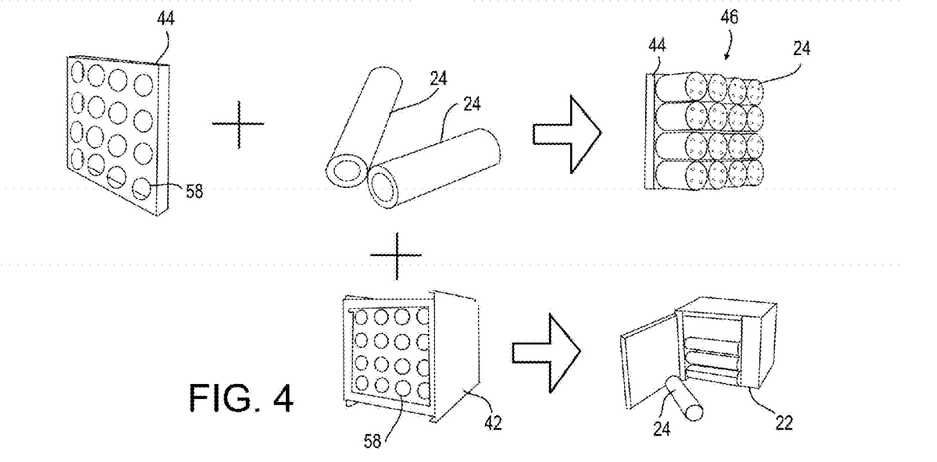
FIG. 4 is a highly schematic view of an installation assembly.

Such a demonstration/evaluation unit 28 may comprise a plasma injector 30 similar to other embodiments described herein. Two examples of such plasma injectors are shown in FIGS. 1 and 4. A control box 32 may comprise the required circuitry and power supply for the demonstration/evaluation unit 28. A blower 34 may be utilized to provide the desired airflow from the inlet 36 from the stack 26 to an outlet 38. The term stack will be used herein to refer to the ducting used to vent "sour" or contaminated gasses in need of filtering or plasma reaction for disinfection purposes. A cabinet 40 may be provided to supply the needed space for catalytic oxidation between the plasma injector 30, and outlet 38. Catalysts for higher concentrations of gasses, for example to oxidize volatile organic compounds (VOC's) or mercaptans may be included in the cabinet 40 or elsewhere in the system. The demonstration/evaluation unit may be utilized to determine the efficiency and power required to reduce the sour gas to an acceptable limit.

In one form, oxidation of odors and formation of PAW occurs in the plasma reactor without an additional supply of chemicals and waste production. The disclosed plasma reaction system may accelerate this process, to reduce unwanted chemicals beyond the stack 26. Since most odor emissions are a unique cocktail (combination) of odor components, the disclosed plasma-injector can apply a dedicated amount of oxidation power for odor control.

Deodorization and disinfection by the disclosed plasma-injector may be facilitated by high-speed oxidation. The oxidized molecules generally cannot be detected organoleptically (by smell), hence they do not bother the observer.

One embodiment of a plasma-injector assembly 22, as shown in one form in FIG. 4, consists of a cabinet 42 with plasma reactors 24 provided therein. Ambient air is radiated there through and, as a result, the oxygen, nitrogen, and water vapor molecules are dissociated.

Figure 6:
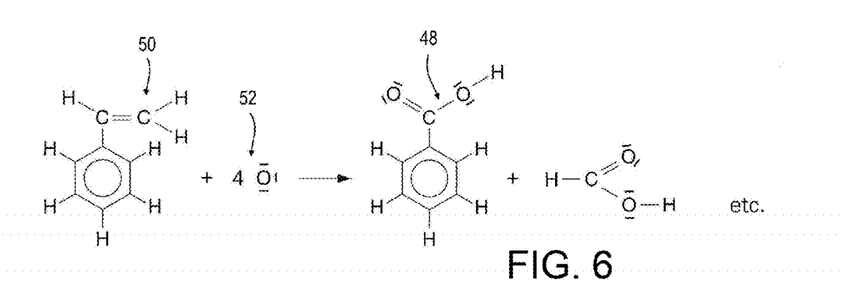
FIG. 6 is a chemical diagram of one use of the disclosed apparatus and system.

This transition (disassociation) may be the first step in a process where extremely reactive PAG and PAW are formed, comprising a mixture of instable oxygen and hydroxyl atoms, ions, radicals etc., with elevated electron energy levels. This gas 52, often called 'active oxygen,' has the ability to execute a high-speed oxidation process 48 with the odor components 50 after injection in the polluted air. Such an oxidation process is shown in FIG. 6. While one particular odor molecule (component) 50 is shown for reference, the proposed apparatus and method operates on many odor molecules.

The odor component 50 will lose the faculty of exciting man's sense of smell through the oxidation process, and thus will not be a nuisance to neighbors or others within the locality of the stack 26.

The plasma-injector system 22, as shown in one form in FIG. 4, utilizes a cabinet 42 with Plasma Reactors 24 positioned therein. Ambient air is radiated there through and as a result, the odor component molecules are dissociated.

In one form, a plurality of plasma reactors 24 are attached to a mounting flange 44 forming a plasma reactor module 46, which is inserted into the cabinet 42, forming a plasma injector 22.

Benefits of the disclosed method and apparatus in several examples include:

High odor removal efficiency with variable power supply 0-100%.
No mechanical wear as there are no moving parts.
No supply of harmful chemicals, absorbents, biomaterial etc.
Substantially no waste.
Relatively low investment and operational costs compared to equivalent processes.
No impact from process fluctuations like dust, temperature, humidity etc.
No impact on the production process.
Does not obstruct process airflow.
Almost no maintenance required, only 1 repair per 3,000 hours of operation.
Lower energy consumption than any other odor control system.
Simple operation (only on/off), no start-up or shut-down procedure.
Modular design, easy to adapt to any airflow.
No exposed high voltage wires or connectors (for example >250V) are present outside the plasma reactor. All high voltage wires and connections are contained safely within the grounded plasma reactor casing.
Very compact, one embodiment of the disclosure has dimensions of W×H×D=0.40×0.70×0.75 m (16×28×30 inch) and operates at 17,000 m3/h (10,000 cfm).

Applications utilizing formed PAW and/or PAG include degradation of:
Bacteria;
Bacterial spores;
Viruses;
Fungi;
Yeast;
Biofilm;
Pesticides, herbicides, algaecides;
Insecticides; and
Chemicals.

Figure 18:
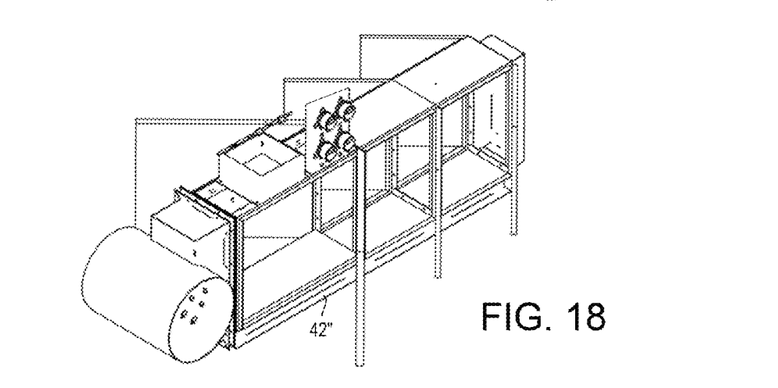
FIG. 18 is a highly schematic view of one mode of use of the disclosure.

Referring still to FIG. 4, filter-holding cabinets 42 are commonly found in the art and field of chemical or obstruction style filters. An implementation utilizing retrofit plasma reactor into an existing cabinet 42 and, in some instances, an existing mounting flange 44 (FIG. 4) results in cost savings, space savings, and other improvements due to the reduced modifications needed to implement the improved design. Looking to FIG. 1, such a retrofit plasma reactor 24 is shown, comprising a bayonet style mounting assembly, so as to be coupled to the mounting flange 44 and substantially aligned with the opening 58 therein. Other mounting structures may also be used, such as threaded or press-fit structures. The mounting flange 44 with the plasma reactors 24 installed therein may then be inserted into the cabinet 42. This results in a cabinet providing in-line plasma filtration, PAW production, and PAG production, or tangential plasma insertion into the process airflow (stack), as shown in the cabinet embodiments 42' and 42" of FIGS. 17 and 18 respectively.

Figure 2:
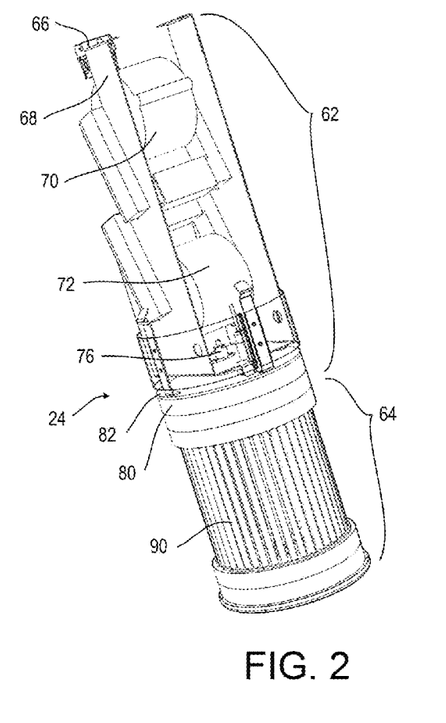
FIG. 2 is an isometric view of the example of FIG. 1 with a portion of the outer casing removed to show the internal components.

Continuing with the description of the example shown in FIG. 1, the outer casing 60 in one form includes an upper unit 62 and a lower unit 64, which may have substantially similar outer shapes and diameters. In one form, an electrical, quick disconnect 66 is provided, which can be seen in more detail in FIG. 3. Once the plasma reactor 24 is in place, the quick disconnect 66 allows for simple electrical connection to a power source and control apparatus. In one form, the lower unit 64 of the outer casing 60 also provides an air conduit, which will be described in more detail. The air conduit in one example generally includes an inlet in the lower portion between the dielectric tubes and the electrode dividers. In one example, a vapor barrier is provided between the lower unit and the upper unit so as to reduce contact of the electronic components from a high humidity environment which is generally detrimental to water and other corrosives. The inlet in one example also comprises perforations or a mesh portion of the outer casing 60 surrounding the lower unit 64. In FIG. 2, the plasma reactor 24 is seen with the outer casing 60 removed from that shown in FIG. 1 to more clearly show the internal components. Particularly, the upper unit 62 is shown comprising the electrical quick disconnect 66 previously described, as well as a transformer bracket 68. An upper transformer 70 and lower transformer 72 are shown physically connected to the transformer bracket 68 and electrically coupled to the electrical quick disconnect 66. While two transformers are shown in this example to provide the desired voltage to the lower unit 64, other arrangements could also be possible. By placing the transformers 70/72 within the outer casing, all voltages outside of the unit can be significantly reduced, increasing the safety parameters of the overall unit. The lower unit 64 is shown connected to the upper unit 62 in a removable manner.

Figure 3:
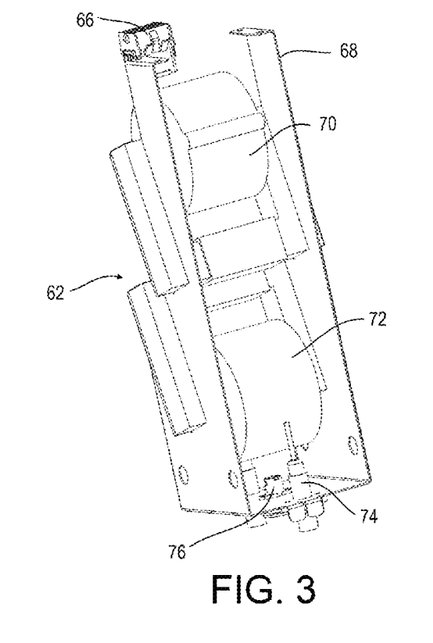
FIG. 3 is an isometric view of an upper unit portion of the example of FIG. 2.

Looking to FIG. 3, the upper unit 62 is shown in more detail, including the components previously described as well as a plurality of female electric couplings 74 and 76, utilized to provide quick electric disconnects between the lower unit 64 and the upper unit 62.

Figure 11:
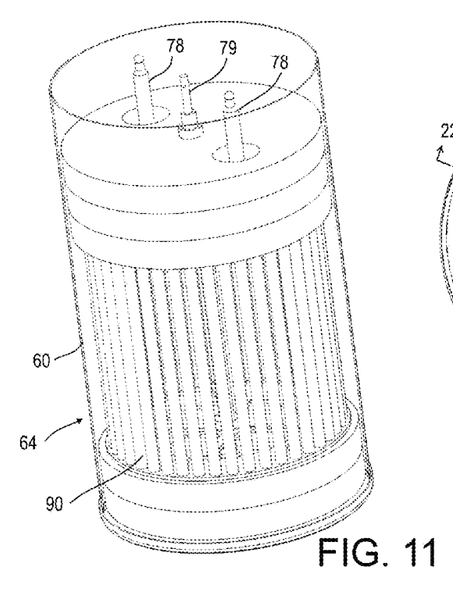
FIG. 11 is an isometric view of a lower unit portion of the example of FIG. 1.
Figure 12:
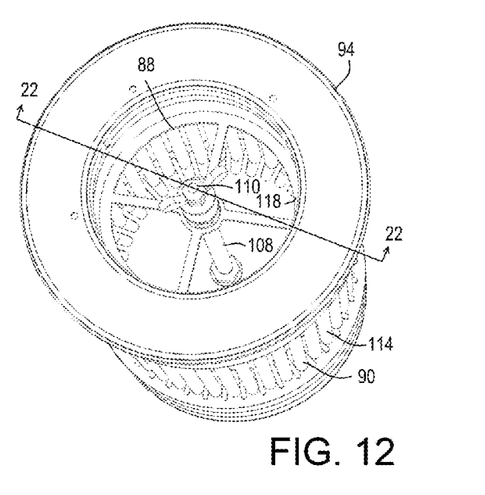
FIG. 12 is another isometric (bottom) view of a lower unit portion of the example of FIG. 1.
Figure 14:
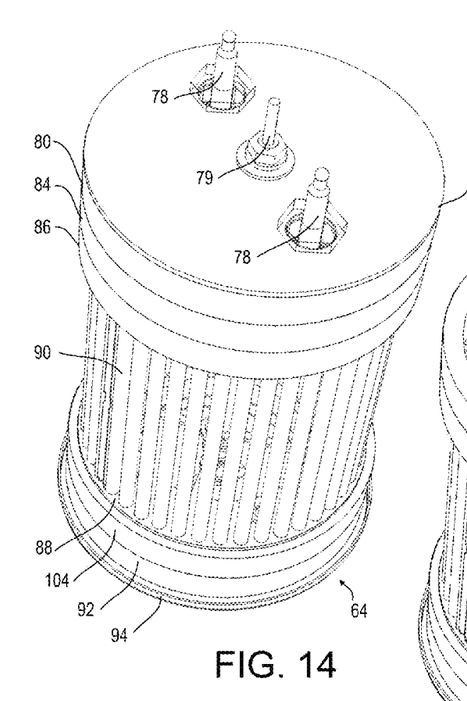
FIG. 14 is an isometric view of a lower unit portion of the example of FIG. 1.
Figure 15:
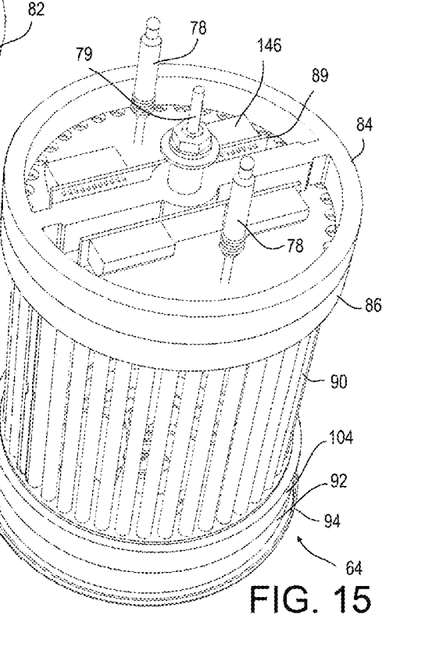
FIG. 15 is an isometric view of a lower unit portion of the example of FIG. 1 with several components removed to show the underlying structure.
Figure 22:
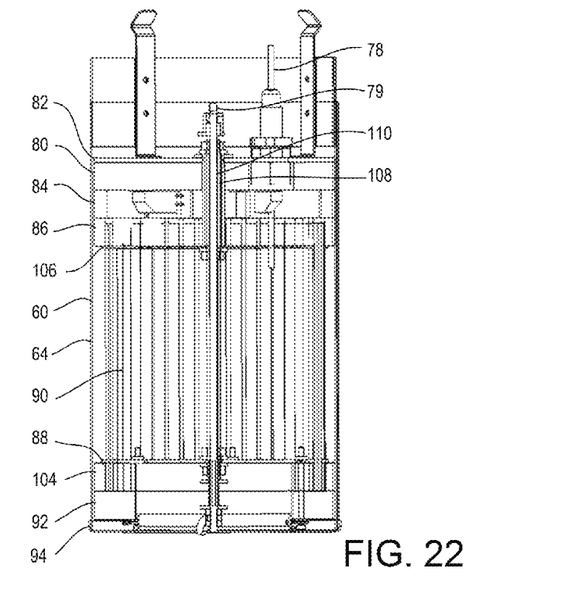
FIG. 22 is a cross sectional view taken along line 22-22 of FIG. 12.

Moving on to FIG. 11, there is shown a more detailed view of the lower unit 64 including a plurality of male electric couplings 78 and 79, which can be utilized in conjunction with the female electric couplings 74 and 76 respectively to complete the quick electric disconnect arrangement between the lower unit 64 and the upper unit 62. In FIG. 11, the lower section of the outer casing is shown generally transparent so as not to obscure viewing of the internal components. In use, a perforated or mesh material may be used to allow airflow through the lower section of the outer casing. FIG. 15 shows a similar view with the outer casing 60 removed, as well as the top cap 80 and connector mounting plate 82, as seen in FIG. 2 or 14. FIG. 15 reveals the structure of the top spacer flange 84 and the top tube adapter 86, which comprises a plurality of surfaces defining voids 89. These voids 89 are utilized to align the dielectric tubes 90, which in this example extend from the top spacer flange 84, through the top tube adapter 86, through a bottom tube adapter plate 88 (See FIG. 22), and through a bottom tube adapter 104 to the bottom cap 92. A bottom cylinder flange 94 may also be provided to align the mesh or perforated portion of the outer casing 60 around the lower unit 64. In one embodiment the top cap 80, top spacer flange 84, top tube adapter 86, bottom tube adapter 104, and bottom cap 92 are formed of a non-conductive material such as ceramic or equivalents. FIG. 15 also shows control circuitry 146 attached to the lower unit 64 within the outer casing.

Figure 19:
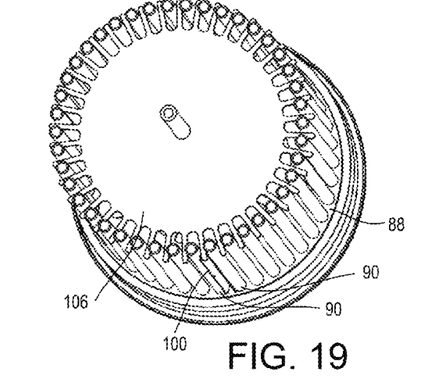
FIG. 19 is an isometric view of a lower unit portion of the example of FIG. 11 with several components removed to show the underlying structure.
Figure 20:
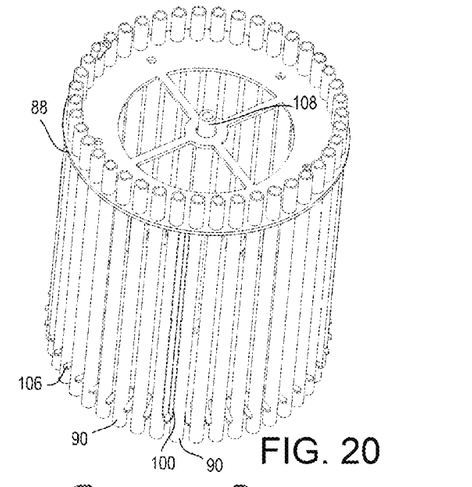
FIG. 20 is an isometric view of a lower unit portion of the example of FIG. 11 with several components removed to show the underlying structure.

FIG. 19 shows several elements removed from the examples shown in FIG. 15. A top tube adapter plate 106 is shown, which extends outward to and contacts each of the electrode dividers 100. In this and other Figs., only one electrode is shown for clarity of illustration, however, it is to be understood that a unique electrode divider 100 would be present between each adjacent dielectric tube 90. At the other end of the lower section is a bottom tube adapter plate 88, which is shown in more detail in FIG. 20. The top tube adapter plate 106 and bottom tube adapter plate 88 indexes, positions, and electrically couples the electrode dividers 100. In one form, the top tube adapter plate 106 and bottom tube adapter plate 88 are formed of stainless steel to facilitate cleaning, provide a ground for the electrode dividers 100, and reduce oxidation. The central rod 110 may in some applications be coupled to the male coupling 79 previously described. The top tube adapter 106 may be made of spring steel.

Figures 16, 17:
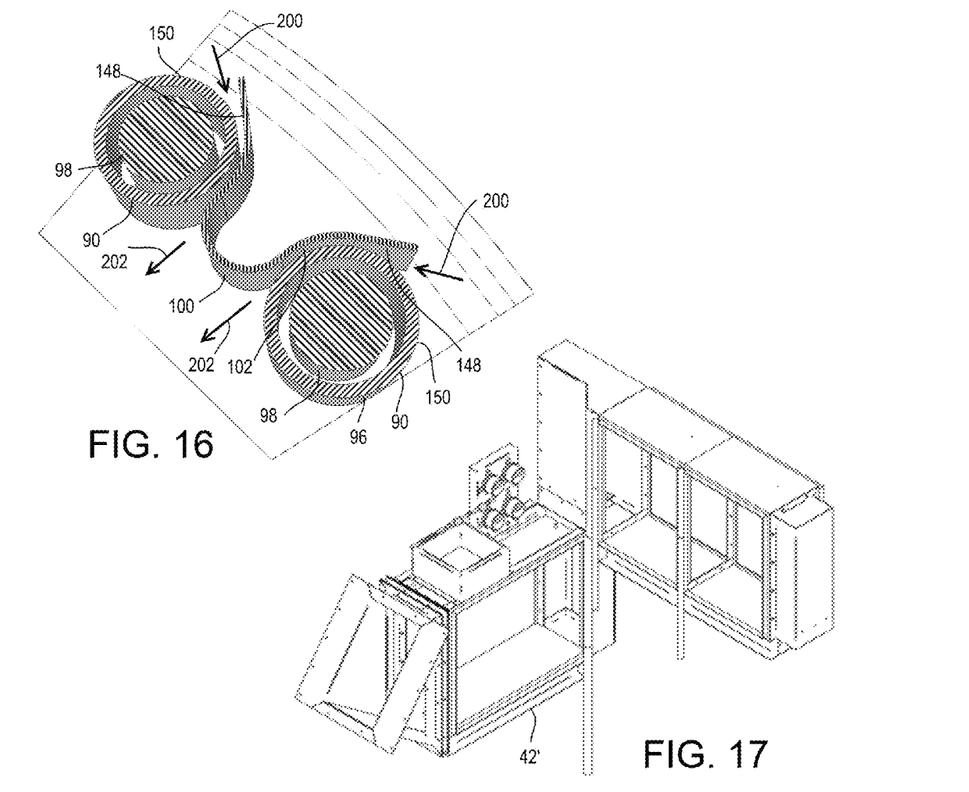
FIG. 16 is a detail view of several internal components of the example of FIG. 1.
FIG. 17 is a highly schematic view of one mode of use of the disclosure.

Looking to FIG. 16, a detail view of the end portion of two dielectric tubes 90 can be seen along with a portion of the outer casing 60. In one form, each dielectric tube 90 comprises a plurality of concentric elements, including an outer non-conductive cylinder 96 and an inner conductive cylinder or rod 98. This view (FIG. 16) is highly schematic and does not necessarily show relative diameters of the individual components. In one form, the non-conductive cylinder 96 is comprised of a ceramic material, although other materials could be used. Within the nonconductive cylinder 96 may be provided a conductive rod or cylinder 98, which is electrically coupled to the transformers 70 and/or 72. To function as a plasma (ozone) or PAW generator, an electrode divider 100 is provided, which is electrically coupled to ground, thus providing a high voltage differential between the conductive rod or cylinder 98 and the electrode divider 100. To provide an air passage between the electrode divider 100 and the dielectric tube 90, a gap 102 is provided. In conjunction with the gap 102, the nonconductive cylinder 96 prohibits arcing and physical contact which would result in electrical conductivity between the conductive rod 98 and the electric divider 100, which would be obviously detrimental to operation as a plasma filter. While the gap 102 is difficult to ascertain from this viewing angle, the gap can be understood by one of ordinary skill in the art.

Figure 21:
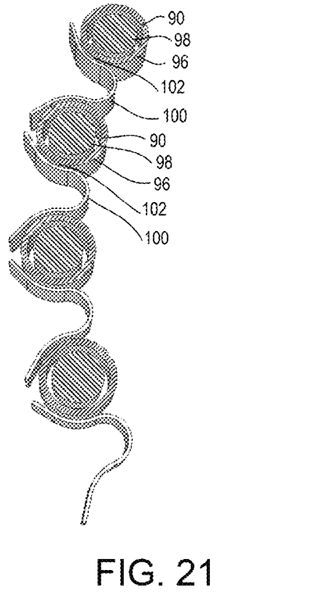
FIG. 21 is an isometric view of a flat (non-cylindrical) example of the disclosure.

The examples of the electric divider 100, shown in FIGS. 16 and 21, are substantially arcuate V-shaped in cross-section. In one example, concave circumferentially outward surfaces 148 of each electric divider 100 face and substantially follow the outer surface 150 of the immediately adjacent dielectric tube 90. This arcuate V-shape allows for a rigid structure with a narrow, substantially linear air gap 102, providing a Venturi effect as fluids flow between the dielectric tube 90 and the adjacent electric divider 100. Previous applications utilizing a flat V-shaped electric divider has less available surface area for discharge and plasma/PAW formation. The previous flat V-shaped electric divider also had less power capacity when used in the same apparatus. The Venturi effect is formed by a large gap between the dielectric tube 90 and the adjacent electric divider 100 at the inlet 200 which narrows toward the median region. The gap may increase again towards the outlet 202. This narrowing of the gap 102 between the dielectric tube 90 and the adjacent electric divider 100 increases speed of, and compress air passing through the gap 102. The Venturi effect is the reduction in fluid pressure that results when a fluid flows through a constricted section of pipe. The Venturi effect is named after Giovanni Battista Venturi (1746-1822), an Italian physicist. The arcuate V-shape generally provides sufficient rigidity to overcome any bending or twisting effects due to movement, placement, or magnetic/gravitational forces. In addition, testing has shown that as air passes through the gap 102 between the cylindrical outer surface of the nonconductive cylinder 96 and the adjacent concave surface of the electrode divider 100, a high velocity air region is created within the discharge zone therebetween. Within this high velocity air region, turbulence is generated in the air currents to improve contact between electrons and the air (gas, vapor), thus the combination of turbulence and high velocity prevents dirt and pollutants from building up on the outer surfaces of the dielectric tube 90 and electrode divider 100. The Venturi effect increases energy efficiency of the apparatus by reducing the pressure drop over the plasma.

Looking to FIG. 5, it can be seen how in this example, humidity controlled ambient air 112 enters the plasma injector 22, and enters the plasma reactor 24 through an inlet 114 which in this embodiment is the mesh/perforated/slotted outer surface of the outer casing 60. The upper unit is not shown in this Example. The air is activated as it passed between the dielectric tubes 90 and electrode dividers 100 previously described, forming PAW and (PAG) which may be collected or directed to solids, liquids gasses (surfaces) to be disinfected. This PAG 116 and PAW then exits the plasma reactor 24 through an outlet 118. In one example, the PAG 116 and PAW are then directed to the stack 26 resulting in fast oxidation of the reactants (odors) in the region 142 within the airflow 28. The PAG 116 and PAW also result in a slow oxidation, with PAW reactive up to a year. This arrangement describes a plasma injector model, which differs from an in-line filtering model in that the process airflow 28 does not pass through the filtering apparatus.

Figure 8:
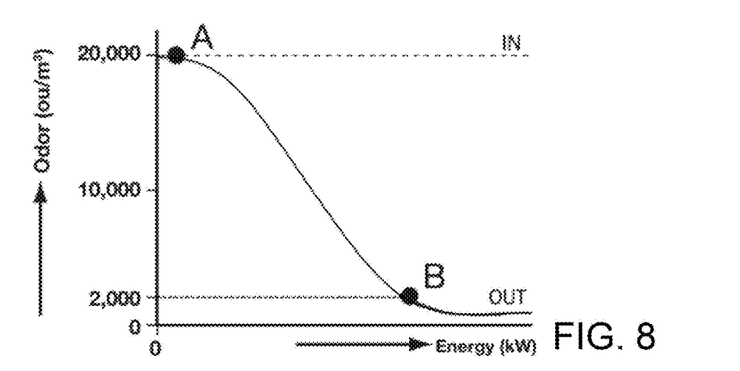
FIG. 8 is a chart which depicts the amount of energy required to decompose odors of differing concentrations.

FIG. 8 shows a graph depicting the amount of energy (plotted on the x-axis) required to filter odor of a particular odor concentration (plotted on the y-axis). Panels of volunteers were used to establish an odor detection threshold.

Figure 9:
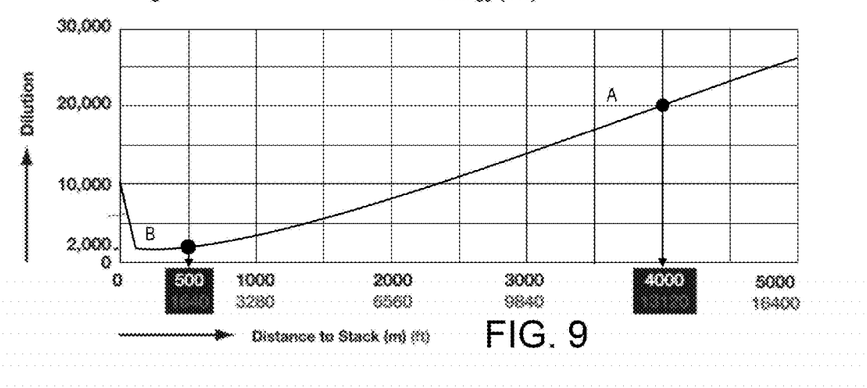
FIG. 9 is a chart which depicts the general relationship between the dilution of an odor as a function of distance to the vent stack.

FIG. 9 shows a graph of a standard dilution versus distance to stack correlation at ground level. The initial slope 140 results from the height of the discharge stack above ground level. The indicator at A shows a detection threshold of an untreated emission at 4,000 meters from the stack. The indicator at B indicates the same odor, wherein the emission is treated, resulting in an odor detection threshold at 500 meters. In simpler terms, the odor of the untreated emission can be detected up to 4,000 meters from the stack, while the treated emission is not organoleptically detectable beyond 500 meters from the stack. This is a result of the decayed odors being much less detectable to a person than the untreated emission. This effect can be very significant where there is a population in the range between 500 meters and 4,000 meters from the stack.

Figure 10:
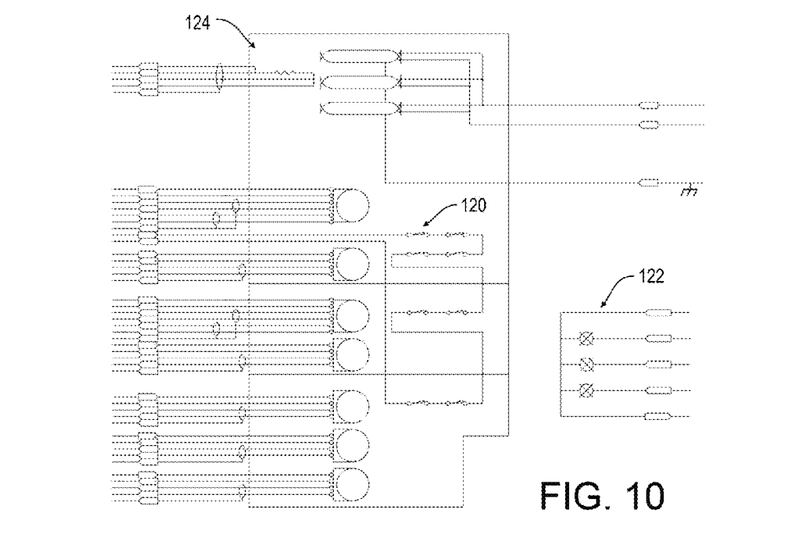
FIG. 10 depicts one example of an electric circuit diagram for a plasma filter cabinet.

FIG. 10 shows the electrical schematic of one example of a cabinet control circuit. Of particular interest are the door switches at 120, which electrically disconnect the transformers when the doors are opened. This added safety feature protects users working on or inspecting the plasma reactors. Another safety feature can be accomplished through the example of FIG. 2 in that the high voltage required for plasma generation is present only within the reactor 24. As the transformers 70 and 72 themselves are within the reactor, all electric contacts and conductor in the cabinet external to the reactor 24 may be of significantly lower and thus safer voltage. Also shown in FIG. 10 is an example utilizing indicators (lights) 122, which indicate the status of the apparatus. A temperature sensor 124 may also be utilized to monitor the temperature of the high voltage transformers as these components may overheat causing faults in the apparatus. Pressure sensors for (ambient injection) air inlet filter(s) may also be utilized. Temperature and humidity sensors may be added to control a humidifier at air intake, if required, to increase hydroxyl and PAW production. Since the high voltage components are insulated, there is no conductive path if condensate/water is present.

Figure 13:
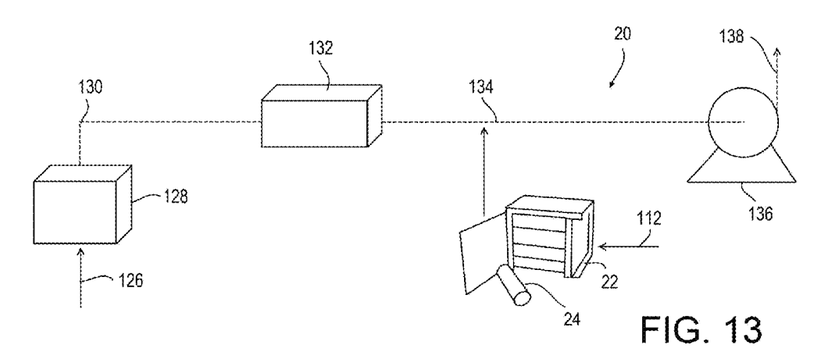
FIG. 13 is a highly schematic flow diagram showing a mode of use of the disclosure.

Looking to FIG. 13, a flow diagram of one embodiment of plasma injector/disinfecting system 20 is shown. The first portions of the system include an ambient air inlet 126 providing air to the process 128. The process may be food packing, processing, manufacturing, or other processes that generate undesired odors and may contain contaminants to be killed in a disinfecting component of the process. The process 128 of this example comprises an outlet 130, which in one form leads to a particle filter 132, such as a cyclone or mesh filter. A plasma injector 22 is shown injecting plasma into the filter outlet 134 where the plasma and PAW reacts with the odors and contaminants therein, which may be vented via an optional catalyst through a blower 136 to atmosphere 138. In a similar example, the plasma injector 22 is provided downstream from the particle filter 132 such that the input air to the plasma injector 22 is filtered. As mentioned, in other applications the particle filter 132 and/or blower 136 may not be utilized.

FIG. 21 shows an example of another relative positioning of the dielectric tubes 90 and electrode dividers 100. As the other components are functionally equivalent, they are not shown in this Fig.

Figure 23:
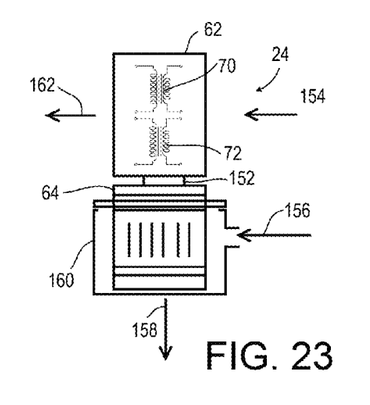
FIG. 23 is a highly schematic view of another application of the plasma reactor.

FIG. 23 shows an example wherein the upper unit 62 of the plasma reactor 24 is separated from the lower unit 64 by way of standoffs 152. This arrangement reduces PAW and plasma from contacting the transformers 70 and 72 within the upper unit 62. Cooling air enters the upper unit at 154, passes the transformers 70 and 72, and exits at 162. The transformer cooling air is independent of process air 156 which enters a chamber 160, passes through the lower unit 64, and exits at 158.

Figure 24:
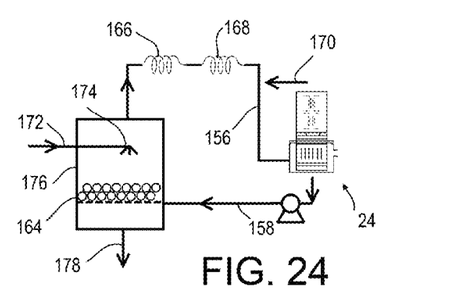
FIG. 24 is a highly schematic view of another application of the plasma reactor.

FIG. 24 shows an example used to treat potentially contaminated matter 164 including liquids (water, juice, milk, etc.) and/or solids (food, feed, surfaces). In this example, the process air 156 input to the plasma reactor 24 as described in reference to FIG. 23 may first be subjected to a dryer/cooler 166 and/or a heater 168 to control temperature and humidity of the process air 156 entering the plasma reactor 24. Cleaning gas and/or liquid 170 such as Oxygen ($O_2$), Nitrogen ($N_2$) Hydrogen Peroxide ($H_2O_2$) Water ($H_2O$) may also be added to the process air 156 upstream or downstream of the dryer/cooler 166, or heater 168 to improve efficiency of the decontamination/disinfection process. In this example of a packed bed, spray tower, or cooling tower reactor is provided a system to mix gas/liquid/solid 164 to contact reactive products (plasma/PAW) from the plasma reactor 24 for disinfection or decontamination.

The matter 164 to be treated may be input 172 at spray nozzle 174 and may exit the chamber 176 at outlet 178.

The example shown in FIG. 24 and others, benefits from the advantage that the matter 164 to be disinfected/decontaminated/treated does not need to be in direct contact with the plasma discharge process (electrons/ions/photons), but that the PAW (vapor or droplets) will transport the reactive oxygen species (ROS), reactive nitrogen species (RNS) present in the PAW together with the reactive species in the gas phase (O3, NOx, etc.). A publicly available 2014 article in the Dublin Institute of Technology ARROW@DIT School of Food Science and Environmental Health written by N. N. Misra, Shashi Kishor Pankaj, Tony Wals, Finbarr O'Regan, and Paula Bourke describes the benefits of PAW exposure as a decontamination method using a rudimentary plasma reactor.

Figure 25:
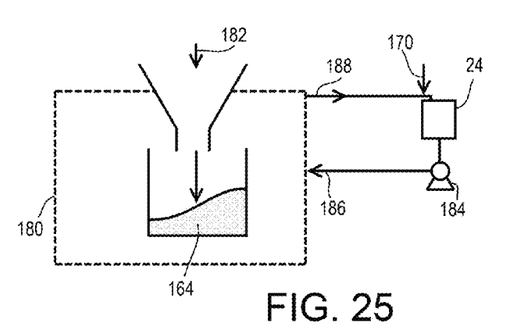
FIG. 25 is a highly schematic view of another application of the plasma reactor.

FIG. 25 shows an in-packaging disinfection apparatus utilizing the plasma reactor 24 previously described, wherein the matter 164 to be treated is placed within an area 180 such as by inserting at matter inlet 182. PAW and other disinfecting products 170 are blown by optional fan 184 through inlet 186 and after reacting with the matter 164, exit the area 180 at outlet 188.

Figure 26:
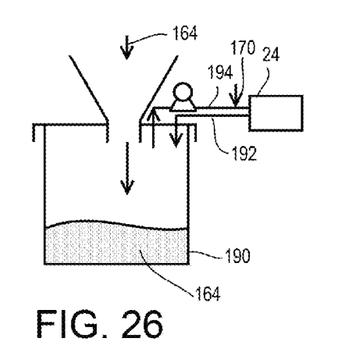
FIG. 26 is a highly schematic view of another application of the plasma reactor.

FIG. 26 shows a treatment apparatus utilizing a bag 190 into which is placed matter 164 to be treated. This apparatus is beneficial in that only the processed air passing through inlet conduit 192 going into the bag 190 need be treated, and this processed air may be returned to the plasma reactor 24 after contact with the material 164 via return conduit 194.

Figure 27:
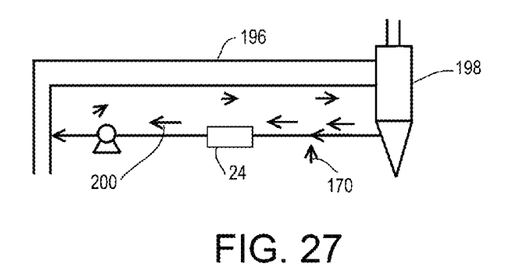
FIG. 27 is a highly schematic view of another application of the plasma reactor.

FIG. 27 shows an example used for surface decontamination of an air duct and cyclone separator. This example utilizes a duct 196 coupled to a cyclone 198 in line with a plasma reactor 24 to direct an airflow of PAW into a surface to be disinfected. Cleaning gas 170 and/or liquid 170 such as Oxygen ($O_2$), Nitrogen ($N_2$) Hydrogen Peroxide ($H_2O_2$) Water ($H_2O$) may also be added to the process air. The treated air and PAW is then circulated into the duct 196 and cyclone separator 198 wherein the treated air and/or PAW is deposited upon interior surfaces therein, disinfecting them as well as any other matter (food, utensils, products, etc.) within the air duct and/or cyclone. As shown, a fraction of the air circulating in the duct 196 and cyclone 198 may be used as process air to increase efficiency. Temperature and humidity control elements may also be incorporated to improve efficiencies.

Testing has shown that PAW may stay reactive for extended periods of time (up to a year in some applications) which may allow for storage of PAW for later use.

The plasma reactor cell 24 can be used as a reactor to generate reactive species (Plasma and PAW for example) to treat contaminants on/in:
- air or gas (in any space: storage room, product-packaging/bags, hospitals, etc.)
- liquids (water, juice, milk, etc.)
- solids (food, feed, skin, etc.)

If required, formation of reactive species can be accomplished with controlling humidity, temperature (controlled condensation on product/surface) and addition of gases/liquids like O2/N2/H2O2/H2O/etc to improve efficiencies.

The humidity can be up to nearly 100% because of the special Venturi shaped airflow design (smooth transition from wide/narrow/wide as shown in FIG. 16) between the dielectric tubes 90 and the electrode dividers 100 for a very high speed air/gas/vapor flow at low pressure drop to prevent a conductive path across the small gas discharge gaps 102 and since the high voltage conductors 98 can be 100% sealed and isolated from the process air/gas/vapor by non-conductive cylinders 96 there is always a proper gas discharge process with little danger of short circuit.

The operating temperature within the plasma reactor 24 can be very high since the reactor may be made of all metal and ceramic parts (including ceramic sealant if required) for maximum temperature. In one application, the operating temperature may be over 800 C to process overheated (superheated) steam/etc. if required. This process can for example be used to inject plasma activated steam into a process like extruders or reactors for food/feed processing and breaking down contaminants (as mentioned above in reference to FIG. 24 for example). The plasma activated steam reactor may further increase pressure of the steam depending on the electrical discharge power applied by increasing temperature within the constant volume plasma reactor. Plasma activated steam can also be used to control humidity in a space or in a process, and control contaminants (as mentioned above) without generation of ozone (or very little) if no oxygen is provided in the process gas or vapor.

Treatment with aqueous ozone (O3 dissolved in water) is well established (sanitation/disinfection/bleaching). The disclosed plasma reactor in several embodiments can be utilized to add more reactive species (plasma and PAW) to aqueous ozone when mixing the PAW flow through aqueous ozone in a spray tower, packed bed or aerator, etc. as shown by example in FIG. 24

The plasma reactor described herein may also be utilized to produce aqueous ozone vapor (or liquid when condensing the vapor in a condenser). The process to such aqueous ozone vapor formulation includes the steps of creating a high concentration of ozone which can be very high (>6,000 ppm) when circulating over a space (increased ozone concentration will be generated when the space is first filled with dry oxygen), followed by adding water vapor.

The plasma reactor and process may further increase reactive species concentration by adding water vapor that contains any concentration of hydrogen peroxide (H2O2) to create extra hydroxyl radicals (OH).

The plasma reactor and process can further increase reactive species concentration by adding air or nitrogen to create high RNS, etc. and may be adjusted with controlling temperature/humidity (condensation on product/surface) until the chemistry is suitable for a desired application.

The process can be accomplished by in-line processing, or with circulating the air/gas/vapor through the plasma reactor to increase the concentration of reactive species. While the present invention is illustrated by description of several embodiments and while the illustrative embodiments are described in detail, it is not the intention of the applicants to restrict or in any way limit the scope of the appended claims to such detail. For example, the terms upper and lower transformer are used to distinguish the separate transformers but the terms are not to be interpreted as relative to gravity or any external reference. Additional advantages and modifications within the scope of the appended claims will readily appear to those sufficed in the art. The invention in its broader aspects is therefore not limited to the specific details, representative apparatus and methods, and illustrative examples shown and described. Accordingly, departures may be made from such details without departing from the spirit or scope of applicants' general concept. For example, the sections (units) 62 and 64 may be attached without a quick disconnect, or the section 62 may be installed in a separate control box. Or a (granular or honeycomb) catalytic converter (catalyst) may be placed between cap 92 and flange 94 to oxidize residual (partially oxidized) gas-contaminates and ozone when the plasma system works in-line. When the ozone is decomposed in this process oxygen radicals are generated that will further oxidize the residual gas contaminates.

Instead of the v-shaped or arcuate v-shaped ground electrodes, the tubes may be alternating high-voltage and grounded electrodes, eliminating the need for the v-shaped or arcuate v-shaped ground electrodes.

Therefore I claim:

1. A plasma reactor assembly comprising:
   a casing comprising;
      a fluid inlet;
      a fluid outlet;
      an electric power input;
   an electric power connector;
   at least one step-up transformer;
   the transformer in electric communication with the electric power connector;
   a plurality of substantially parallel cylindrical, hollow, dielectric tubes having a longitudinal axis, each dielectric tube in electric communication with the transformer;
   at least one arcuate v-shaped electrode divider positioned between each dielectric tube with an fluid gap between each electrode divider and each adjacent dielectric tube,
   a voltage differential between each dielectric tube and each electrode divider; and;
   wherein there is no fluid path between the fluid inlet and the fluid outlet except between the dielectric tubes and the electrode dividers.

2. The plasma reactor assembly as recited in claim 1 wherein each dielectric tube in turn comprises:
   an outer ceramic tube;
   an inner metal electrode tube surrounded in a plane orthogonal to the longitudinal axis of the dielectric tube by the outer ceramic tube; and
   a central high voltage lead surrounded in a plane orthogonal to the longitudinal axis of the dielectric tube by the inner metal electrode tube.

3. The plasma reactor assembly as recited in claim 1 wherein the casing comprises:
   an upper unit containing the transformer bracket and transformers therein;
   a lower unit comprising the dielectric tubes and the electrode dividers therewithin, and;

a releasable physical connection and a releasable electrical connection there between the upper unit and the lower unit.

4. The plasma reactor assembly as recited in claim 1 wherein the casing comprises a first half of a bayonet style coupling operatively configured to couple to a second half of the bayonet style coupling which is provided on a cabinet housing.

5. The plasma reactor assembly as recited in claim 4 further comprising:
a cabinet door, and;
an door switch operatively configured to allow electricity to be provided to the electric power inlet of the outer casing only when the cabinet door is closed.

6. The plasma reactor assembly as recited in claim 1 wherein each transformer comprises a high frequency, high voltage output to the dielectric tubes.

7. The plasma reactor assembly as recited in claim 1 wherein the casing has a shape and size identical to the housing of an existing chemical or barrier filter to provide a retrofit thereto when electrically connected to a power source.

8. The plasma reactor assembly as recited in claim 1 wherein:
the fluid inlet and fluid outlet of the casing is in-line with a vent stack of a production process to treat the fluid passing there through by way of rapid oxidation.

9. The plasma reactor assembly as recited in claim 1 wherein the fluid outlet of the casing is tangential to a vent stack of a production process to provide plasma into the vent stack which in turn reacts with the fluid passing there through by way of rapid oxidation.

10. The plasma reactor assembly as recited in claim 1 wherein the fluid outlet of the outer casing in fluid communication with a chemical reaction or catalyst filter selected from chemical reaction filters which are regenerated by contact with ozone produced by the dielectric tubes.

11. The plasma reactor assembly as recited in claim 1 wherein the outer casing is substantially cylindrical.

12. A method for replacing a chemical or barrier filter with a plasma reactor assembly, the method comprising the steps of:
providing plasma reactor having an outer casing comprising;
a fluid inlet;
a fluid outlet;
an electric power input;
an electric power connector;
providing a transformer bracket coupled to the outer casing;
providing at least one step-up transformer attached to the transformer bracket in electric communication with the electric power connector;
providing a plurality of substantially parallel, cylindrical, hollow, dielectric tubes having a longitudinal axis, each dielectric tube in electric communication with the transformer;
providing at least one arcuate v-shaped electrode divider positioned between each dielectric tube with a fluid gap between each electrode divider and each adjacent dielectric tube,
a voltage differential between each dielectric tube and each electrode divider;
wherein there is no fluid path between the fluid inlet and the fluid outlet except between the dielectric tubes and the electrode dividers;
removing an existing chemical or barrier filter;
installing the plasma reactor into the space vacated by the removed chemical or barrier filter; and
connecting a power supply to the plasma reactor.

13. A method for disinfecting or sanitizing comprising the steps of:
providing a casing comprising;
a fluid inlet;
a fluid outlet;
an electric power input;
an electric power connector;
providing at least one step-up transformer in electric communication with the electric power connector;
providing a plurality of substantially parallel, cylindrical, hollow, dielectric tubes having a longitudinal axis, each dielectric tube in electric communication with the transformer;
providing at least one arcuate v-shaped electrode divider positioned between each dielectric tube with a fluid gap there between,
a voltage differential between each dielectric tube and each electrode divider and;
wherein there is no fluid path between the fluid inlet and the fluid outlet except between the dielectric tubes and the electrode dividers;
directing a fluid output of the fluid outlet to matter to be disinfected.

14. The method for disinfecting as recited in claim 13 further comprising a step of manipulating the humidity of fluid entering the fluid inlet.

15. The method for disinfecting as recited in claim 13 further comprising the step of adding reactants to the fluid inlet or fluid outlet selected from the list consisting of Oxygen (O2), Nitrogen (N2), Hydrogen Peroxide (H2O2), and Water (H2O).

16. The method for disinfecting as recited in claim 13 further comprising the step of controlling the temperature of the fluid output.

17. The method for disinfecting as recited in claim 13 wherein the disinfecting step includes the step of applying the fluid output to chemicals for improved oxidation.

* * * * *